(12) United States Patent
Krol et al.

(10) Patent No.: US 9,933,244 B2
(45) Date of Patent: Apr. 3, 2018

(54) REDUCED BACK REFLECTION OPTICAL COHERENCE TOMOGRAPHY PROBE

(71) Applicant: Corning Incorporated, Corning, NY (US)

(72) Inventors: Mark Francis Krol, Painted Post, NY (US); William James Miller, Horseheads, NY (US); Robert Adam Modavis, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 117 days.

(21) Appl. No.: 14/997,834

(22) Filed: Jan. 18, 2016

(65) Prior Publication Data

US 2016/0370168 A1 Dec. 22, 2016

Related U.S. Application Data

(60) Provisional application No. 62/180,701, filed on Jun. 17, 2015.

(51) Int. Cl.
*G01B 9/02* (2006.01)
*G02B 27/09* (2006.01)
(Continued)

(52) U.S. Cl.
CPC ........ *G01B 9/02034* (2013.01); *A61B 5/0066* (2013.01); *A61B 5/0084* (2013.01); *G01B 9/0205* (2013.01); *G01B 9/02091* (2013.01); *G02B 6/4214* (2013.01); *G02B 27/0994* (2013.01)

(58) Field of Classification Search
CPC .............. G01B 9/02091; G02B 27/005; G02B 27/0911; G02B 27/0955; G02B 27/0977; G02B 27/0994; G02B 6/2552; G02B 6/26; G02B 6/262; G02B 6/32; G02B 6/327; G02B 6/4204; G02B 6/4206; G02B 6/4214; G01D 5/35374; A61B 5/0066; A61B 5/0068; A61B 5/6852; A61B 5/6876; A61B 5/0071; A61B 5/0084; A61B 5/02007
USPC ... 385/27–28, 31, 33, 39, 53, 78, 79, 88–92, 385/116–117, 119, 902; 600/160, 170, (Continued)

(56) References Cited

U.S. PATENT DOCUMENTS 5,940,554 A 8/1999 Chang et al.
7,024,078 B2 4/2006 Knox
(Continued)

FOREIGN PATENT DOCUMENTS

CN 203263350 U 11/2013

OTHER PUBLICATIONS

International Search Report and Written Opinion PCT/US2016/037958 dated Sep. 9, 2016.

*Primary Examiner* — Akm Enayet Ullah
*Assistant Examiner* — Michael Mooney
(74) *Attorney, Agent, or Firm* — Svetlana Z. Short

(57) ABSTRACT

A beam-shaping optical system suitable for use with optical coherence tomography including a sheath defining a central cavity, a beam-shaping insert defining a beam-shaping element positioned within the central cavity, and an optical fiber having a core and a cladding. The optical fiber defines an angularly prepared fiber end configured to emit an electromagnetic beam toward the beam-shaping element with the core of the optical fiber locally expanded at the fiber end.

25 Claims, 12 Drawing Sheets

(51) Int. Cl.
*G02B 6/42* (2006.01)
*A61B 5/00* (2006.01)

(58) Field of Classification Search
USPC ......... 600/342, 407, 425, 473–479; 356/456, 356/477, 479, 484–48
See application file for complete search history.

(56) References Cited

U.S. PATENT DOCUMENTS

| | | | |
|---|---|---|---|
| 8,861,900 B2* | 10/2014 | Bhagavatula | A61B 5/0066 385/12 |
| 8,967,885 B2* | 3/2015 | Bhagavatula | G02B 6/2552 385/93 |
| 9,025,158 B2 | 5/2015 | Froggatt et al. | |
| 9,404,731 B2* | 8/2016 | Adler | A61B 5/0066 |
| 2004/0109164 A1 | 6/2004 | Horii et al. | |
| 2005/0143664 A1 | 6/2005 | Chen et al. | |
| 2006/0132790 A1 | 6/2006 | Gutin | |
| 2010/0228238 A1 | 9/2010 | Brennan et al. | |
| 2011/0178409 A1 | 7/2011 | Harris et al. | |
| 2013/0331709 A1* | 12/2013 | Le | G02B 6/32 600/478 |
| 2014/0276108 A1* | 9/2014 | Vertikov | A61B 5/0084 600/478 |
| 2017/0205256 A1* | 7/2017 | Kim | G01D 5/35374 |

* cited by examiner

REDUCED BACK REFLECTION OPTICAL COHERENCE TOMOGRAPHY PROBE

This application claims the benefit of priority under 35 U.S.C. § 119 of U.S. Provisional Application Ser. No. 62/180,701 filed on Jun. 17, 2015, the content of which is relied upon and incorporated herein by reference in its entirety.

BACKGROUND

The present disclosure relates to optical coherence tomography, and in particular, to a beam-shaping optical probe for an optical coherence tomography probe having reduced back reflection.

Optical coherence tomography (OCT) is used to capture a high-resolution cross-sectional image of biological tissues and is based on fiber-optic interferometry. The core of an OCT system is typically a Michelson or Mach-Zehnder interferometer. For simplicity, only a basic Michelson interferometer is disclosed which typically includes a first optical fiber which is used as a reference arm and a second optical fiber which is used as a sample arm. The sample arm includes the sample to be analyzed, as well as a probe that contains optical components therein. A light source upstream of the probe provides light used in imaging. A photodetector is arranged in the optical path downstream of the sample and reference arms. The probe is used to direct light into and/or onto the sample and then to collect scattered light from the sample.

Optical interference of light from the sample arm and the reference arm is detected by the photodetector only when the optical path difference between the two arms is within the coherence length of the light from the light source. Depth information from the sample is acquired by axially varying the optical path length of the reference arm and detecting the interference between light from the reference arm and scattered light from the sample arm. A three-dimensional image is obtained by transversely scanning in two dimensions the optical path in the sample arm. The axial/depth range of the process is determined by the coherence length and spectral bandwidth, while the overall transverse resolution is dictated by the size of the image spot formed by the optical components of the probe.

Because the probe typically needs to be inserted into a small cavity of the body, generally it must be small and preferably have a simple optical design. Exemplary designs for the probe include a transparent cylinder in which the miniature probe optical components are contained and through which light is transmitted and received. However, light may be lost due to back reflection when it passes through materials having a different refractive index, thus decreasing image spot intensity. Additionally, unwanted back reflections decrease the signal to noise ratio in the data. Moreover, having multiple and separate optical components in the probe is generally problematic because the small optical components have to be assembled and aligned, which adds to the cost and complexity of manufacturing the probe.

SUMMARY

According to one embodiment of the present disclosure, a beam-shaping optical system suitable for use with optical coherence tomography includes a sheath defining a central cavity, a beam-shaping insert defining a beam-shaping element positioned within the central cavity, and an optical fiber having a core and a cladding. The optical fiber defines an angularly prepared fiber end configured to emit an electromagnetic beam toward the beam-shaping element with the core of the optical fiber locally expanded at the fiber end.

According to another embodiment of the present disclosure, an optical coherence tomography probe includes a sheath defining a central cavity and an optical fiber having a core and a cladding positioned within a ferrule with the ferrule positioned within the central cavity. An electromagnetic beam is emitted from a fiber end of the optical fiber toward a beam-shaping element. The fiber end is tapered relative to the optical fiber to produce a mode field diameter of between about 10 microns and about 40 microns at a beam wavelength of 1310 nanometers.

According to another aspect of the present disclosure, a method of operating an optical coherence tomography probe using an optical fiber includes the steps of positioning an optical fiber within a central cavity of a sheath, positioning a beam-shaping element within the sheath, transmitting an electromagnetic beam from a fiber end of the optical fiber into the beam-shaping element, and receiving a back reflection from the electromagnetic beam of less than about −100 dB.

According to another aspect of the present disclosure, an optical coherence tomography probe includes a sheath defining a central cavity and an opening, an optical fiber having a core and a cladding positioned within a ferrule, the ferrule positioned within the central cavity of the sheath, and a torque tube having an exterior surface and a solid end, the solid end having a reduced portion configured to mate with the opening.

According to another aspect of the present disclosure, an optical coherence tomography probe including a sheath defining a central cavity and an opening, a beam-shaping insert defining a beam-shaping element positioned within the central cavity, a torque tube having a solid end, the solid end defining an aperture, a reinforcing liner positioned within both the sheath and the solid end of the torque tube, and an optical fiber passing though the reinforcing liner, the optical fiber having a core and a cladding.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiments, and together with the description serve to explain principles and operation of the various embodiments.

DETAILED DESCRIPTION

Figure 1A:
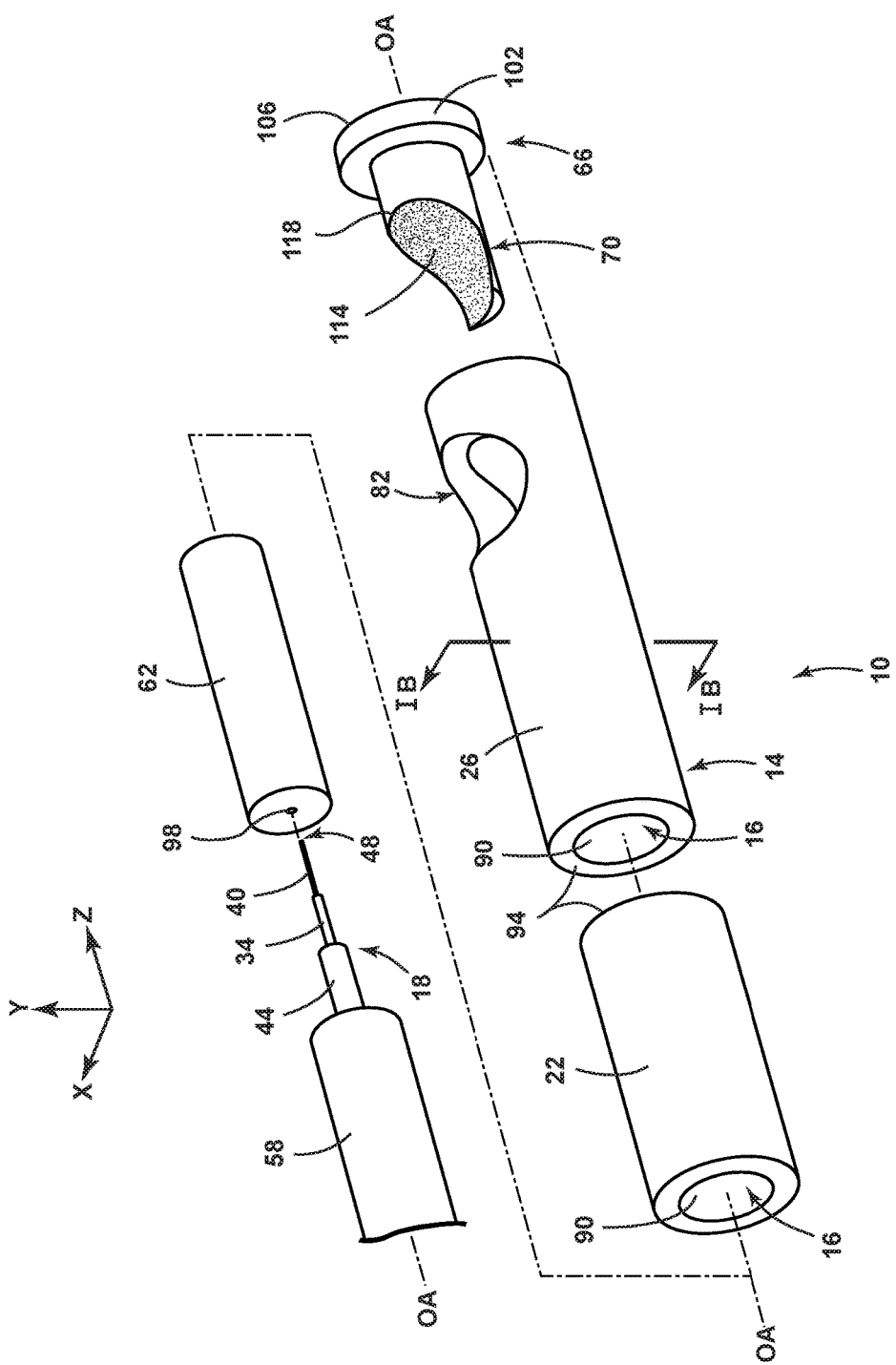
FIG. 1A is an elevated exploded view of an optical probe for use in OCT according to one embodiment.

Reference will now be made in detail to the present preferred embodiments, examples of which are illustrated in the accompanying drawings. Whenever possible, the same reference numerals will be used throughout the drawings to refer to the same or like parts.

For purposes of description herein, the terms "upper," "lower," "right," "left," "rear," "front," "vertical," "horizontal," and derivates thereof shall relate to an optical probe 10 as oriented in FIG. 1A, unless stated otherwise. However, it is to be understood that the optical probe 10 may assume various alternative orientations, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Depicted in FIGS. 1A-8 is an embodiment of the beam-shaping optical probe 10 suitable for use in OCT and the making of OCT images. The optical probe 10 includes a sheath 14 defining a central cavity 16 within which an optical fiber 18 is disposed. The sheath 14 is comprised of a first portion 22 and a second portion 26. The optical fiber 18 includes a cladding 34, a core 40, and a coating 44. In various embodiments the coating 44 is polymeric, but may also comprise metal. The optical fiber 18 includes a fiber end 48 configured to emit an electromagnetic beam 52. The electromagnetic beam 52 may be a light beam (e.g., visible, ultraviolet, infrared or light). The electromagnetic beam 52 is emitted along an optical axis OA defined by the optical probe 10. In assembly, the optical fiber 18 enters the optical probe 10 through a torque tube 58 and is coupled to a ferrule 62. A beam-shaping insert 66 is positioned at a distal end of the optical probe 10 and defines a beam-shaping element 70.

Figure 1B:
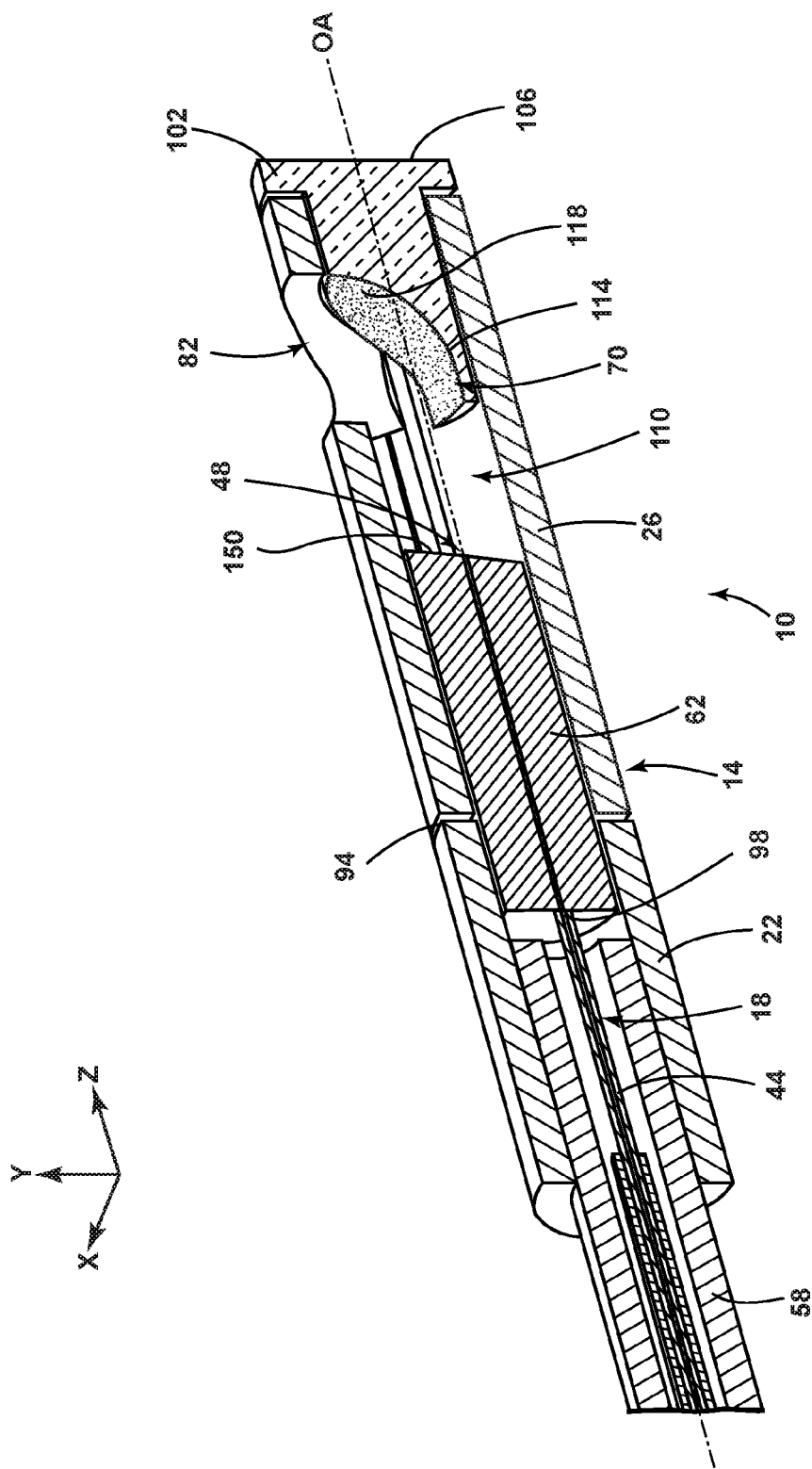
FIG. 1B is an elevated perspective cross-sectional view of the optical probe depicted in FIG. 1A in assembly taken at line IB-IB of FIG. 1A according to one embodiment.

Referring now to FIGS. 1A and 1B, the sheath 14 is an assembly of the first portion 22 and the second portion 26 aligned on axis OA and in abutment with one another. In the depicted embodiment, the second portion 26 defines a window 82 through which the electromagnetic beam 52 (FIG. 5) may exit and enter the optical probe 10. Optionally, the window 82 may include a transparent material through which the electromagnetic beam 52 can pass, yet prevents foreign matter from entering the optical probe 10. The sheath 14 may comprise a transparent or opaque material at a wavelength utilized by the electromagnetic beam 52. In some embodiments the sheath 14 may comprise a polymeric material such as latex, polyethylene, or polyurethane or a metal such as 304 or 306 stainless steel. The central cavity 16 of the sheath 14 is defined by an inner wall 90. The first and second portions 22, 26 each define an abutment surface 94 configured to be in contact or close proximity when the optical probe 10 is in the assembled configuration. The ferrule 62, the torque tube 58 and the beam-shaping insert 66 are shaped to precisely mirror the inner wall 90 of the sheath 14 such that the ferrule 62, torque tube 58 and the beam-shaping insert 66 precisely fit within the central cavity 16 in a flush and substantially concentric manner. In assembly, the optical fiber 18 travels through the torque tube 58 from an upstream light source (not shown) to the ferrule 62. The ferrule 62 defines an aperture 98 extending though the ferrule 62 into which the optical fiber 18 is positioned. The aperture 98 is configured to accept the cladding 34 and the core 40 of the optical fiber 18. By positioning the optical fiber 18 within the ferrule 62, a central axis of the fiber 18 along which the electromagnetic beam 52 is emitted may be quickly aligned to the optical axis OA of the optical probe 10 due to the high concentricity between the ferrule 62 and the inner wall 90 of the probe 10.

The beam-shaping insert 66 is configured to be inserted into the central cavity 16 of the distal end of the sheath 14 such that a flange 102 is in abutting contact with the sheath 14. The beam-shaping insert 66 may be bonded in place mechanically or chemically (e.g., adhesively or with an epoxy). It will be understood that various embodiments of the optical probe 10 and beam-shaping insert 66 do not necessarily have a flange 102. The flange 102 is positioned on the beam-shaping insert 66 such that the flange 102 contacts the second portion 26 of the sheath 14 as the beam-shaping element 70 is positioned proximate the window 82. In this manner, the flange 102 may aid in the positioning of the beam-shaping insert 66 within the sheath 14 as well as the beam-shaping element 70. Optionally, a forward surface 106 of the beam-shaping insert 66 and/or the flange 102 includes one or more markings (e.g., degree dial, an index line, hash marks) designed to aid an operator in correctly orienting the beam-shaping insert 66 within the sheath 14. Additionally or alternatively, the sheath 14 (e.g., second portion 26) may include the same, similar, or complimentary markings configured to aid in orientation of the beam-shaping insert 66. Orientation of the beam-shaping insert 66 within the sheath 14 is performed such that the beam-shaping element 70 is aligned with the optical axis OA of the optical probe 10 and the window 82 of the sheath 14. A gap 110 is defined between the ferrule 62 and the beam-shaping insert 66 when in assembly. In various embodiments, the beam-shaping insert 66 and/or the ferrule 62 includes a polymeric composition. Exemplary polymeric materials for the beam-shaping insert 66 include ZEONOR® (available from Zeon Chemicals L.P., Louisville, Ky.), polyetherimide (PEI), polyethylene, polypropylene, polycarbonate, engineered polymers (e.g., liquid crystal), as well as any other polymeric material or combination of polymeric materials capable of forming the beam-shaping insert 66 and producing a smooth surface. In other embodiments, the beam-shaping insert 66 may include metals, ceramics, or composites thereof. The beam-shaping insert 66 and/or the ferrule 62 is capable of formation by conventional manufacturing techniques such as injection molding, casting, machining, thermoforming, or extrusion.

Still referring to FIGS. 1A and 1B, the beam-shaping element 70 is integrally defined by the beam-shaping insert 66 such that in assembly, the beam-shaping element 70 is positioned inside of the central cavity 16 of the sheath 14. The beam-shaping element 70 includes a reflective element 114 positioned on a curved surface 118 defined from the beam-shaping insert 66. The beam-shaping insert 66 extends in an upwardly and inwardly curved manner with respect to the forward surface 106 to define the curved surface 118. The beam-shaping element 70 is substantially conic in shape and curves inwardly toward the optical axis OA of the optical probe 10. The conic shape of the beam-shaping element 70 is defined by a radius of curvature and conic constant along an axis of the beam-shaping element 70 with respect to the optical axis OA of the optical probe 10.

In order to properly shape the electromagnetic beam 52, the beam-shaping element 70 may have a radius of curvature along the X-axis that is the same or different than a radius of curvature in the Y-axis. The radius of curvature of the X- and Y-axes of the curved surface 118 of the beam-shaping element 70 may have an absolute value of between about 0.5 millimeters and about 10 millimeters, and more specifically, about 1.0 millimeter to about 4.0 millimeters. The conic constant of the X- and Y-axes of the beam-shaping element 70 may independently range from about 1 to about −2, and more specifically between about 0 and about −1. It should be understood that the radii and conic constants of the curved surface 118 explained above describe the overall shape of the beam-shaping element 70, and do not necessarily reflect local radii or conic constants of the curved surface 118. The radius of curvature of the X-axis and Y-axis of the beam-shaping element 70 may be adjusted independently in order to correct for any material disposed around the optical probe 10. The conic shape of the beam-shaping element 70 may be decentered along the Y- or Z-axes between about 0.01 millimeters and about 0.8 millimeters. Additionally, the conic shape of the beam-shaping element 70 may have a rotation between the Y- and Z-axes of between about 70° and 120°.

The beam-shaping element 70 is configured to collect and shape (e.g., collimate, converge, and/or change the optical path of) through reflection the electromagnetic beam 52 (FIG. 5) emitted from the optical fiber 18, as explained in greater detail below. Positioned on the curved surface 118 of the beam-shaping element 70 is the reflective element 114. The reflective element 114 may comprise a dielectric coating, a metal coating, or an enhanced metal coating. Exemplary metal coatings include silver, gold, aluminum, platinum and other lustrous metals capable of reflecting the beam 52. Dielectric coatings may include one or more dielectric stack having alternating layers of $SiO_2$ and at least one of $Ta_2O_5$, $NbO_5$, $TiO_2$, and HfO2. Further, enhanced metal coatings may include a combination of one or more of the previously described metals and/or dielectrics. For example, the reflective element 114 may include a base layer of silver with one or more dielectric stacks positioned thereon. The reflective element 114 may also include a capping layer to protect it from environmental conditions (e.g., water, oxygen, and/or sterilization procedures). Additionally or alternatively, the reflective element 114 may include a barrier layer. The barrier layer may serve to both adhere the reflective element 114 to the curved surface 118 of the beam-shaping insert 66 as well as protect the beam-shaping insert 66 from damage in high power embodiments of the electromagnetic beam 52. The barrier layer may comprise layers of chromium, aluminum, and alumina, each layer having a thickness of between about 10 nm and about 50 nm. The reflective element 114 is positioned on the beam-shaping element 70 such that the emitted beam 52 is reflected externally to the beam-shaping insert 66, and not within it.

Figure 2:
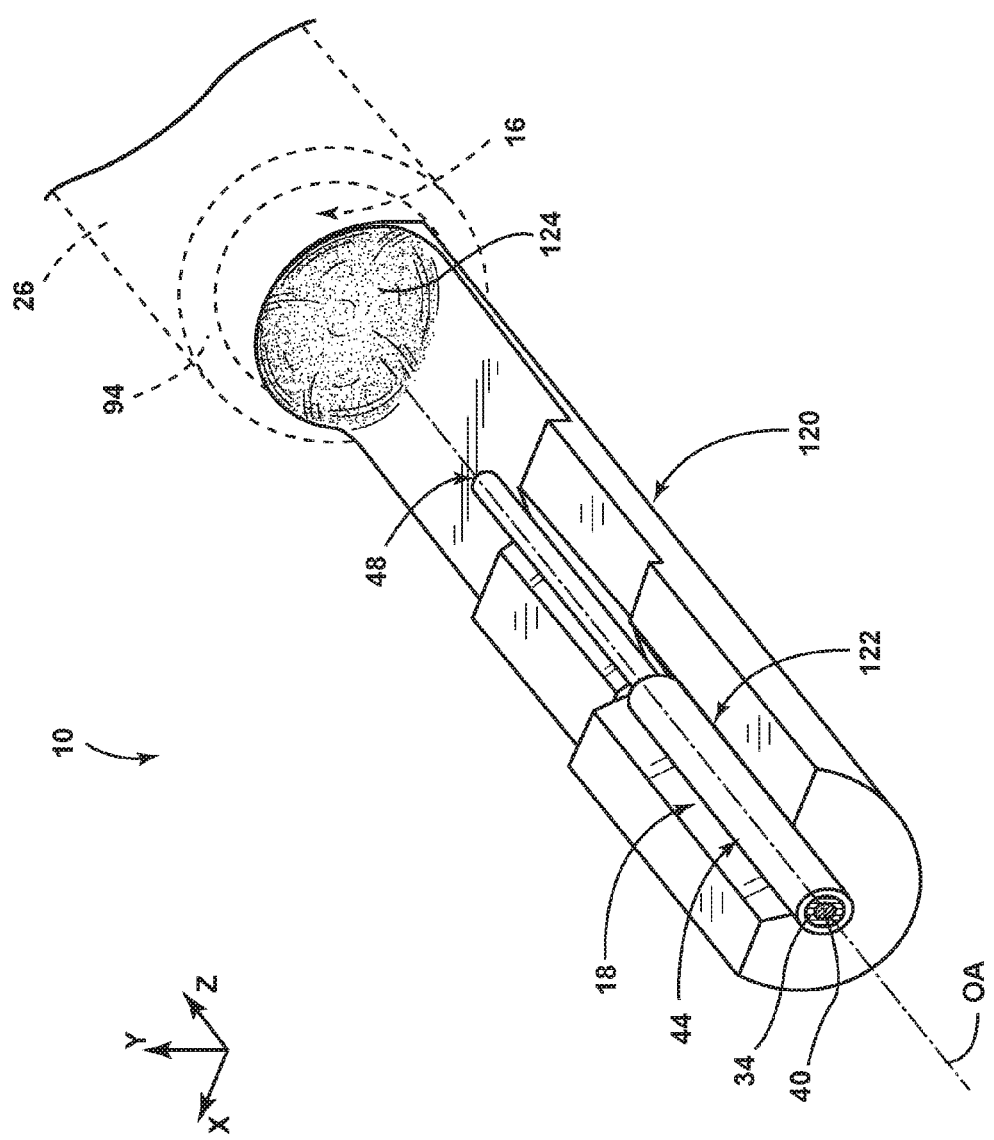
FIG. 2 is an elevated partially exploded view of the optical probe depicted according to another embodiment.

Referring now to FIG. 2, depicted is an embodiment of the optical probe 10 in which the ferrule 62 and the beam-shaping insert 66 may be replaced with a monolithic body 120 in which the optical fiber 18 is positioned. The monolithic body 120 defines an alignment feature 122 into which the optical fiber 18 is positioned. The fiber end 48 of the optical fiber 18 is depicted as protruding from the alignment feature 122, but may also be supported on top of the alignment feature 122. The monolithic body 120 defines a beam-shaping feature 124. The beam-shaping feature 124 may be assembled and function in a substantially similar manner to that of the beam-shaping element 70 of the beam-shaping insert 66. The monolithic body 120 may be inserted into the sheath 14 (e.g., the first or second portions 22, 26) such that the beam-shaping feature 124 is positioned under the window 82 (FIG. 1B). The monolithic body 120 may then be secured in place via an adhesive or epoxy.

Figure 3A:
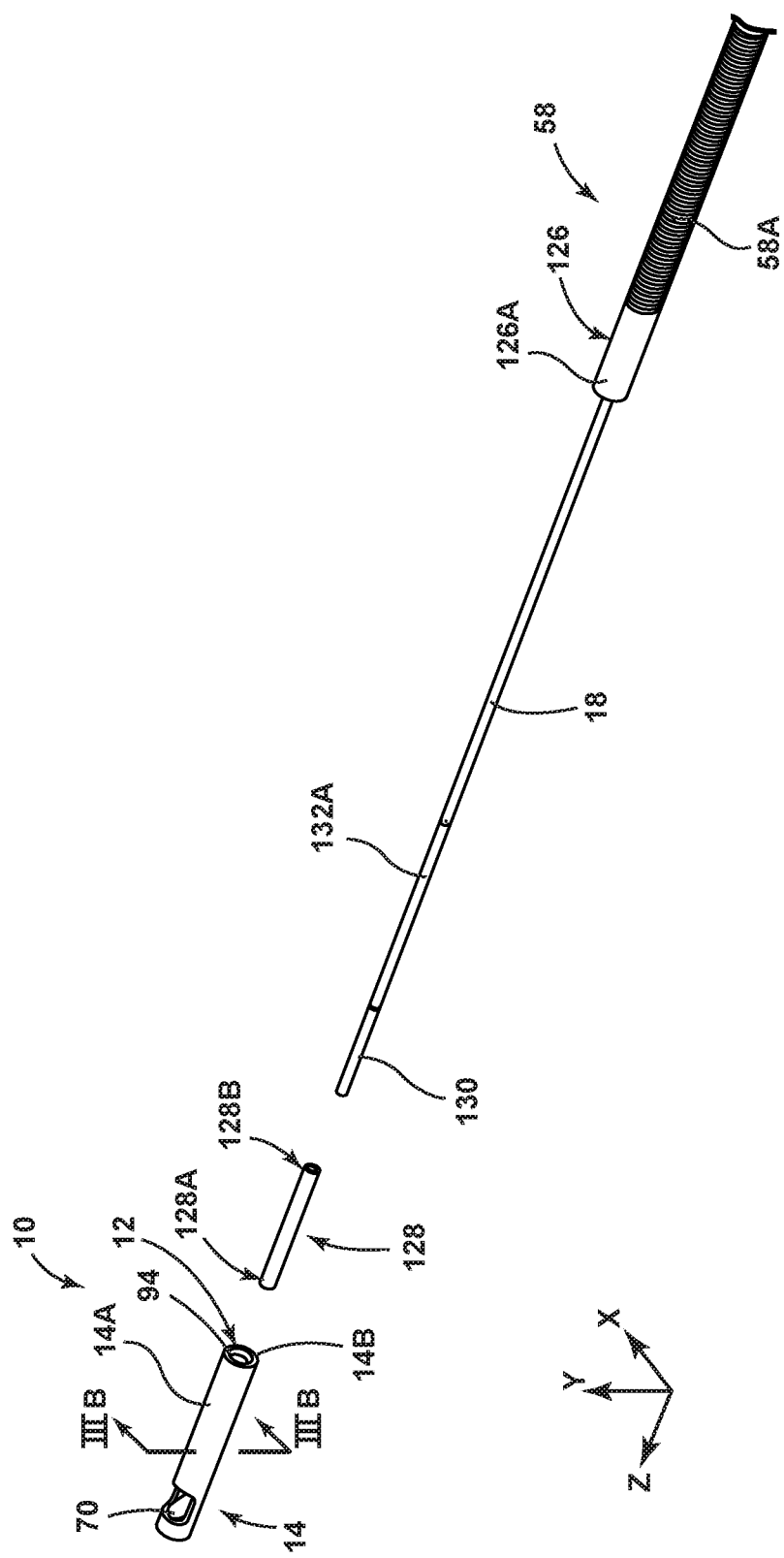
FIG. 3A is an elevated exploded view of the optical probe according to another embodiment.
Figure 3B:
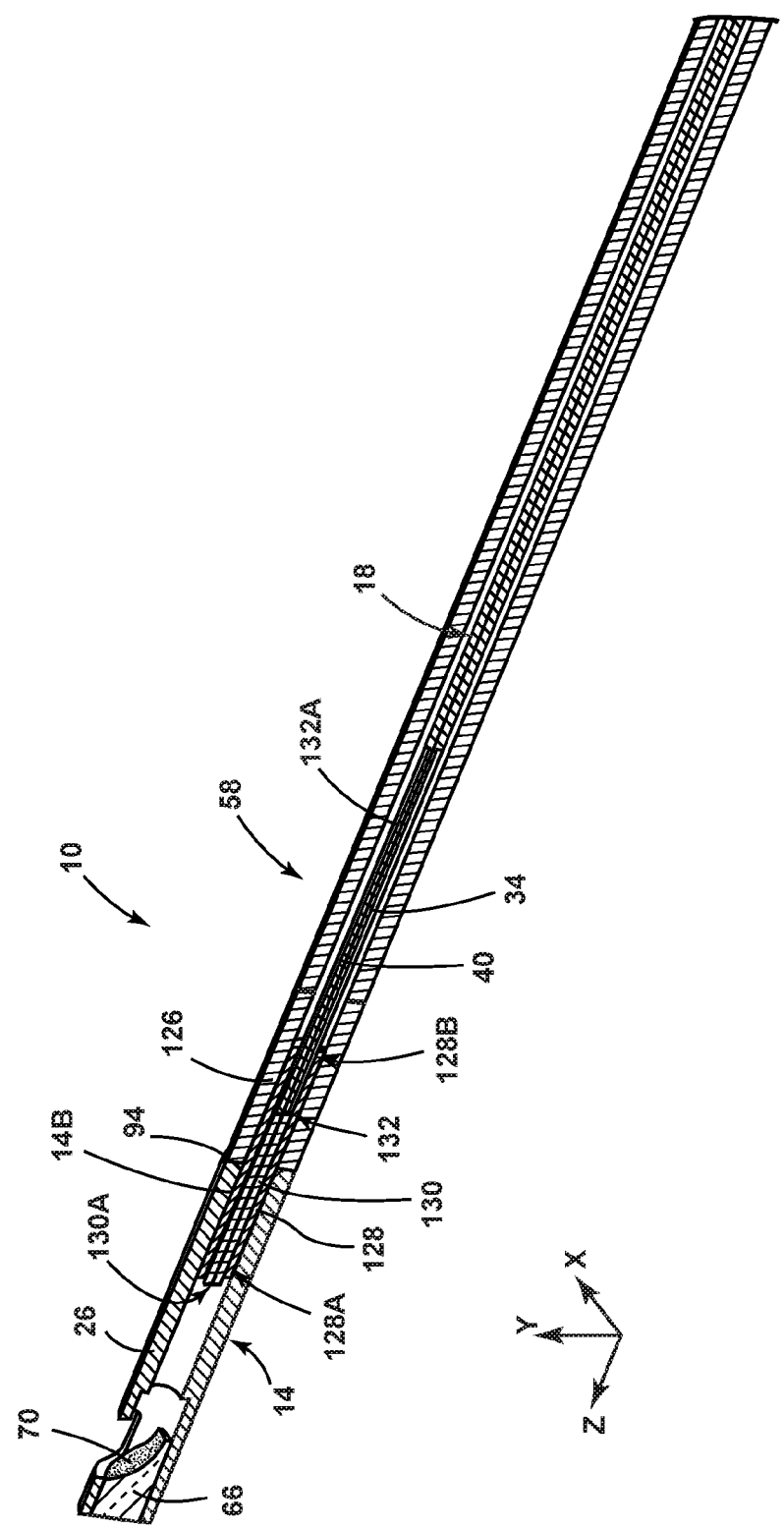
FIG. 3B is an elevated perspective cross-sectional view of the optical probe depicted in FIG. 3A in assembly taken at line IIIB-IIIB of FIG. 3A according to one embodiment.

Referring now to FIGS. 3A and 3B, depicted is an embodiment of the optical probe 10 in which the sheath 14 is a unitary body (e.g., just the second portion 26) defining an opening 12 and the torque tube 58 does not enter the sheath 14. In such an embodiment, a solid end 126 of the torque tube 58 abuts the abutment surface 94 of the second portion 26 of the sheath 14 such that a sheath surface 14A may be flush with a solid surface 126A of the solid end 126. The solid end 126 is formed on an end of the torque tube 58 and may comprise a plastic, metal, ceramic or composite material. The solid end 126 may be formed on the torque tube 58 in a variety of methods including soldering (e.g., silver or tin), welding, brazing, laser welding, over molding (e.g., injection molding) and in some embodiments via epoxy. Disposed within both the sheath 14 and the solid end 126 of the torque tube 58 is a reinforcement liner 128. The reinforcement liner 128 includes both a distal end 128A and a proximal end 128B. Positioned within the reinforcement liner 128 are the optical fiber 18 and a large fiber 130. The large fiber 130 and the optical fiber 18 may be joined via a splice 132 positioned within the reinforcement liner 128. The splice 132 may be accomplished via a fusion splicer, resistant heating, or other methods of optical fiber joining Surrounding the splice 132 and extending over the optical fiber 18 and the large fiber 130 is a splice coating 132A. The splice coating 132A may comprise a polymeric material configured to aid in protecting the optical fiber 18, the large fiber 130 and the splice 132 from damage. In some embodiments, the splice coating 132A is substantially similar to that of the coating 44.

Referring now to FIG. 3B, the large fiber 130 may have a core and a cladding similar to that of the optical fiber 18. In one embodiment, the core of the large fiber 130 is approximately the same diameter as that of the core 40 of the optical fiber 18 and the cladding of the large fiber 130 may have a greater thickness than the cladding 34 of the optical fiber 18. In other words, the large fiber 130 may have a larger outer diameter than the optical fiber 18. During joining of the large fiber 130 and the optical fiber 18, the core 40 and cladding 34 of the optical fiber 18 and the core and the cladding of the large fiber 130, respectively, are joined at the splice 132. The large fiber 130 may define a large fiber end 130A, similar to that of the fiber end 48 of the optical fiber 18, which may be configured to emit the electromagnetic beam 52. It will be understood that in embodiments incorporating the large fiber 130, the large fiber end 130A may be utilized in the same or a substantially similar manner to that disclosed in connection with the fiber end 48.

In assembly, the distal end 128A of the reinforcement liner 128 is positioned within the sheath 14, and the proximal end 128B is positioned within the solid end 126 of the torque tube 58. The reinforcement liner 128 may comprise a metal, a polymer or a ceramic material. While depicted as substantially cylindrical, the reinforcement liner 128 may take a variety of shapes configured to mate with the sheath 14 and the solid end 126. In some embodiments, an inner diameter of the solid end 126 may be smaller than a nominal inner diameter of the sheath 14. In such embodiments, an outer diameter of the reinforcement liner 128 may be sized to fit an inner diameter of the solid end 126 while the sheath 14 may define a raised lip 14B sized to match the inner diameter of the solid end 126. The inner diameter of the reinforcement liner 128 may be substantially constant from the distal end 128A to the proximal end 128B and may be about the size of the outer diameter of the large fiber 130 plus the thickness of the splice coating 132A. In assembly, a gap may be formed around the optical fiber 18 proximate the proximal end 128B of the reinforcement liner 128 due to the disparity in outer diameters of the large fiber 130 and the optical fiber 18. The gap may be filled with an adhesive or an epoxy to provide structural stability to the optical probe 10 in addition to providing strain relief to the optical fiber 18.

Use of the large fiber 130 and the reinforcement liner 128 may provide a variety of manufacturing and use benefits to the optical probe 10. For example, in various embodiments, use of the reinforcement liner 128 and the large fiber 30 may eliminate the need for a ferrule having a specialty or uncommon sizing, thus decreasing the expense of manufacturing. Generally, control of the diameter of an optical fiber is cheaper and easier to do than procuring a specialty sized ferrule requiring micron level precision. Accordingly, by replacing a ferrule with the large fiber 130 a cost savings may be realized. Additionally, by utilizing the reinforcement liner 128, the solid surface 126A and an exterior surface 58A of the torque tube 58 may align in a flush manner with the sheath surface 14A. Embodiments where the torque tube 58 is smaller than and/or positioned inside the sheath 14 may result in a wobbling of the torque tube 58 inside of an interlumen as the optical probe 10 is spun. Wobbling of the torque tube 58 may result in distortion of an OCT image formed by the optical probe 10. Orienting the torque tube 58 and the sheath 14 such that the exterior surface 58A, the solid surface 126A, and the sheath surface 14A are all substantially flush, or have minimal offset relative to one another, decreases the distortion experienced by the probe 10. Further, use of the reinforcement liner 128 may provide a pull strength to the optical probe 10 greater than about 1 kg, greater than about 5 kg, and greater than about 10 kg pull strength.

Figure 4A:
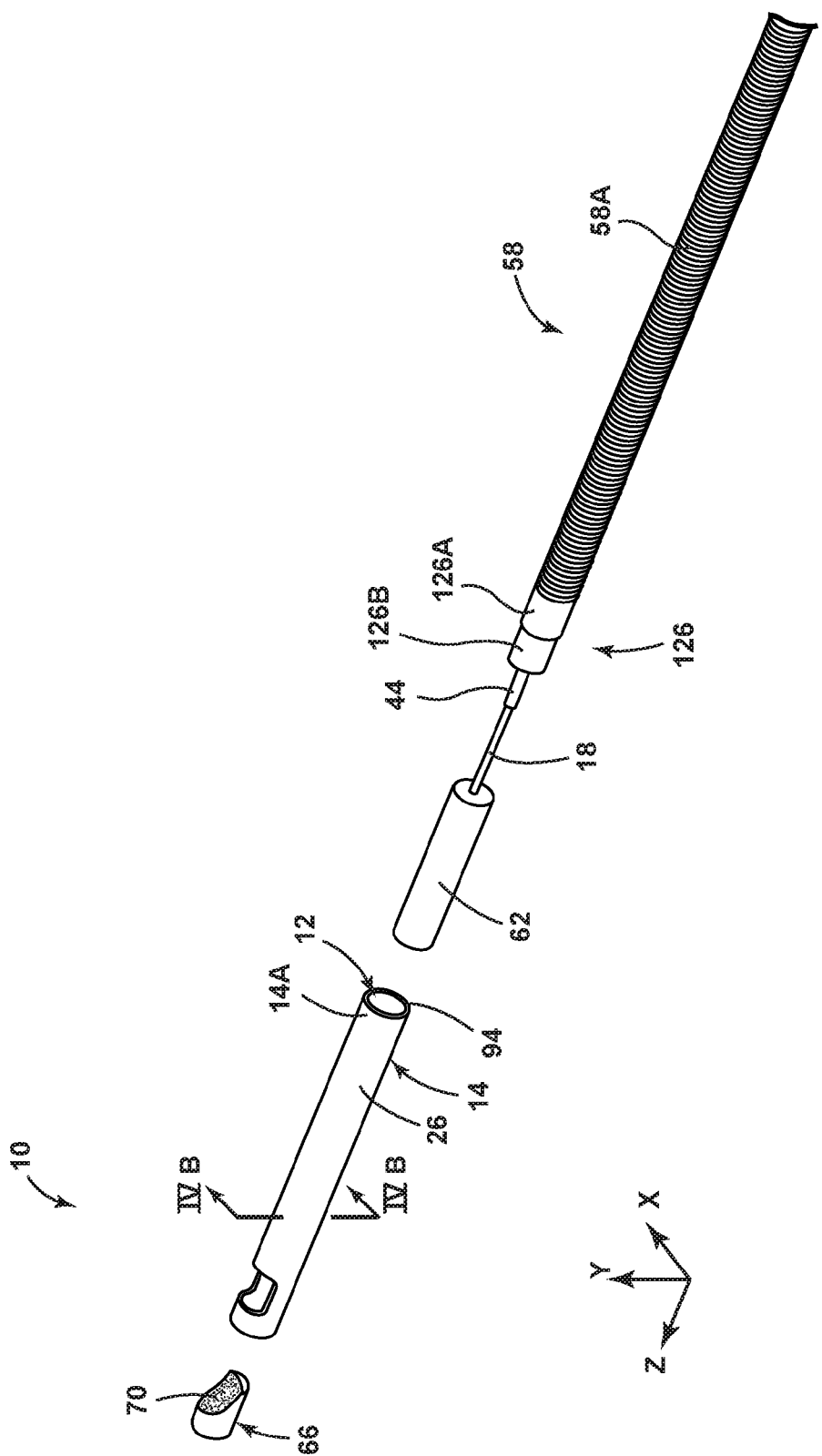
FIG. 4A is an elevated exploded view of the optical probe according to another embodiment.
Figure 4B:
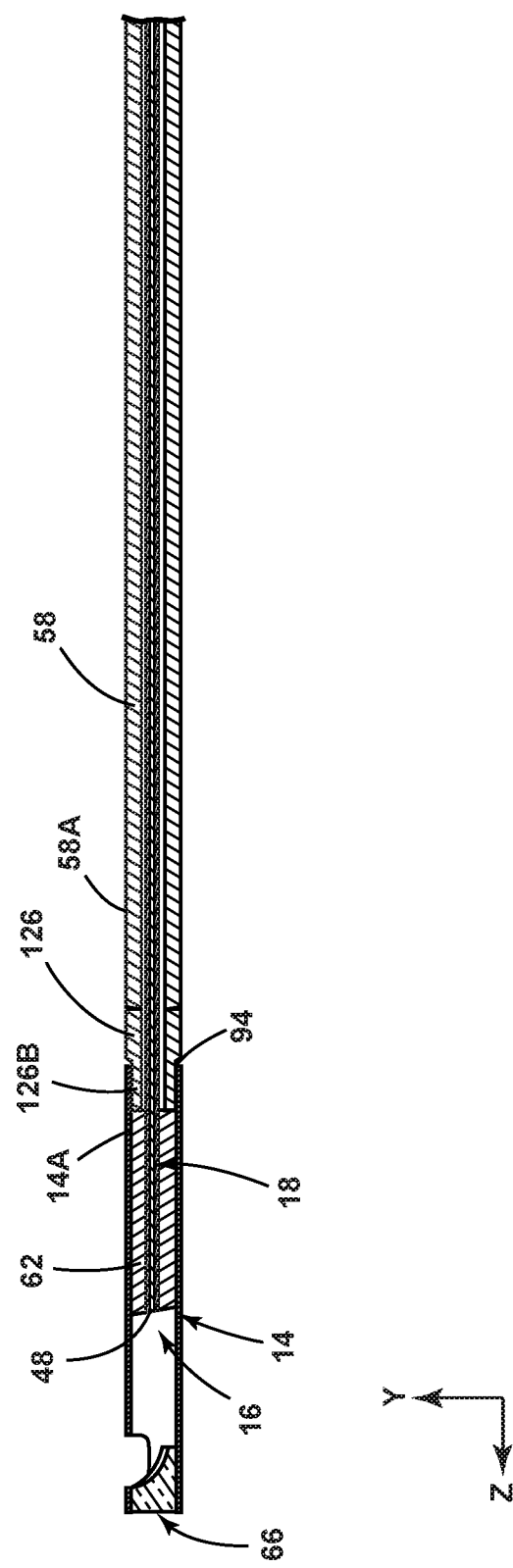
FIG. 4B is an elevated perspective cross-sectional view of the optical probe depicted in FIG. 4A in assembly taken at line IVB-IVB of FIG. 4A according to one embodiment.

Referring now to the depicted embodiment of FIGS. 4A and 4B, the exterior surface 58A of the torque tube 58 and the sheath surface 14A may be substantially flush with one another without the use of the reinforcement liner 128 (FIGS. 3A and 3B). In such an embodiment, the sheath 14 may be a single piece part (e.g., only portion 26) or multi-piece part (e.g., first and second portions 22, 26). The solid end 126 of the torque tube 58 is depicted as including a reduced portion 126B which is dimensionally smaller than the solid end 126. The reduced portion 126B may have an aperture through which the optical fiber 18 may pass. In embodiments where the solid end 126 is cylindrical, the reduced portion 126B may also be cylindrical in shape and have a smaller diameter than the solid end 126. It will be understood that the reduced portion 126B may have a different shape (e.g., square, cuboid, triangular, or star-shaped) than that that of the solid end 126. The solid end 126 may have an outer diameter between about 0.5 millimeters and about 2.0 millimeters, or between about 0.7 millimeters and about 1.3 millimeters. In a specific embodiment, the outer diameter of the solid end 126 may be about 1.0 millimeter. In various embodiments, the outer diameter of the solid end 126 is substantially similar to the outer diameter of the sheath 14. The reduced portion 126B, in cylindrical embodiments, may have an outer diameter between about 0.3 millimeters and about 1.6 millimeters, or between about 0.6 millimeters and about 1.0 millimeter. In a specific embodiment, the outer diameter of the reduced portion may be about 0.8 millimeters. In various embodiments, the outer diameter of the reduced portion 126B may be substantially similar to that of the inner diameter of the sheath 14 (i.e., the diameter of the central cavity 16) and the outer diameter of the ferrule 62. In embodiments where the reduced portion 126B is integrally defined by the solid end 126, the reduced portion 126B may be produced through a variety of machining methods including step grinding, milling, laser cutting or other suitable machining techniques. In alternative embodiments, the reduced portion 126B may be a separate component coupled to the torque tube 58 mechanically or chemically (e.g., adhesively, with an epoxy, or welding). In yet other embodiments, the reduced portion 126B may be formed on the solid end 126 via over-molding. In various embodiments, the reduced portion 126B may be comprised of a different material (e.g., metal, polymer, or ceramic).

Referring now to FIG. 4B, in assembly, the reduced portion 126B of the solid end 126 is configured to mate with the sheath 14 such that the exterior surface 58A of the torque tube 58 and the sheath surface 14A are substantially flush with minimal (e.g., 50 microns or less, or 10 microns or less, or 5 microns or less) to no offset. In one exemplary assembly method, the optical fiber 18 is run through the torque tube 58 and exits the solid end 126. A portion (e.g., between about 1 millimeter and about 4 millimeters) of the optical fiber 18 is then stripped of its coating 44 and any fiber end 48 treatments (as explained in greater detail blow) are performed. The ferrule 62 is then placed over the optical fiber 18 portion not having the coating 44 and is coupled in place via an adhesive, an epoxy, or other suitable coupling method. The torque tube 58 is then used to position the ferrule 62 into the central cavity 16 of the sheath 14. The torque tube 58 may then be used to adjust at least one of a rotation or positional location of the ferrule 62 in the Z direction along the optical axis OA of the optical probe 10. Once in position, the reduced portion 126B may be mechanically or chemically bonded (e.g., via epoxy) to the sheath 14. In various embodiments, relative sizes of the solid end 126 and the reduced portion 126B are configured to mate with the opening 12 and the abutment surface 94 of the sheath 14 such that ferrule 62 and optical fiber 18 are positioned correctly within the central cavity 16 when the solid end 126 contacts the abutment surface 94.

Use of the reduced portion 126B of the solid end 126 may provide a variety of manufacturing and use benefits to the optical probe 10. As explained above, embodiments where the torque tube 58 is smaller than and/or positioned inside the sheath 14 may result in a distortion of an OCT image formed by the optical probe 10 due to wobbling. By utilizing the reduced portion 126B to mate with the sheath 14 such that the exterior surface 58A, the solid surface 126A, and the sheath surface 14A are all substantially flush, or have a minimal offset relative to one another, a decrease in the distortion experienced by the probe 10 during operation may be achieved. Further, by reducing the total part count of the optical probe 10, tighter tolerances and a decreased manufacturing expense for the optical probe 10 may be achieved.

Figure 5:
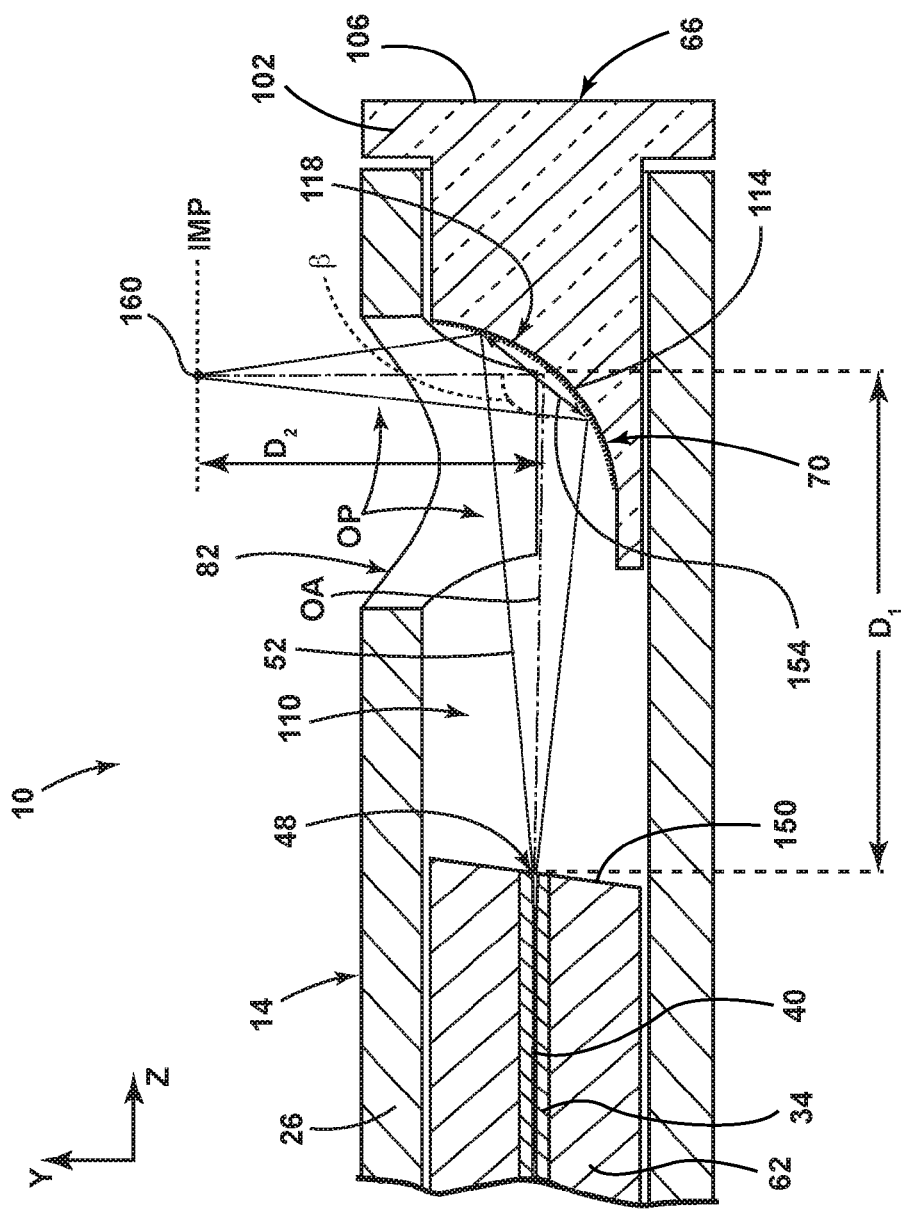
FIG. 5 is a partial enlarged cross-sectional view of the optical probe taken at line IB-IB of FIG. 1A according to one embodiment.

Referring now to FIG. 5, the optical fiber 18 is depicted as defining the fiber end 48 flush with a face 150 of the ferrule 62. In operation, the optical fiber 18 is configured to act as a wave guide for electromagnetic radiation, specifically light at an operating wavelength $\lambda$. The optical fiber 18 carries light from an upstream light source (not shown) to the fiber end 48 where the light is emitted as the electromagnetic beam 52. In one embodiment, the operating wavelength $\lambda$ includes an infrared wavelength such as one in the range from about 850 nanometers to about 1,600 nanometers, with exemplary operating wavelengths $\lambda$ being about 1300 nanometers and about 1560 nanometers. In various embodiments, the operating wavelengths $\lambda$ may be as low as about 700 nanometers. The optical fiber 18 may be a single mode or a multimode configuration. The optical fiber 18 may have a mode field diameter of between about 9.2 microns+/−0.4 microns at a wavelength of 1310 nanometers and have a mode field diameter of about 10.4 microns+/−0.5 microns at 1550 nanometers. The diameter of the cladding 34 may be between about 120 microns and about 130 microns.

The ferrule 62 is configured to couple with the inner wall 90 of the sheath 14 such that when the optical fiber 18 is within the aperture 98, the electromagnetic beam 52 is emitted from the fiber end 48 on an optical path OP that is both substantially coaxial with the optical axis OA of the optical probe 10, and directed toward the beam-shaping element 70. As the beam 52 is emitted from the fiber end 48, it propagates through the gap 110 and the diameter of the optical path OP widens with increasing distance from the fiber end 48. A distance $D_1$ between the fiber end 48 and the reflective element 114 of the beam-shaping element 70 is set based on a desired size of a beam spot 154. The beam spot 154 is the area of light the electromagnetic beam 52 forms as it strikes the beam-shaping element 70. The beam spot 154 grows in diameter with increasing distance $D_1$ from the fiber end 48. In order for the beam-shaping element 70 to properly shape the electromagnetic beam 52, the beam spot 154 must be have the proper diameter when contacting the reflective element 114 (e.g., approximately half the diameter of the reflective element 114). Accordingly, the ferrule 62 and the fiber end 48 must be placed a predetermined distance from the beam-shaping element 70 for the beam 52 to be properly shaped. In various embodiments, the distance $D_1$ between the fiber end 48 and the reflective element 114 may range between about 0.2 millimeters and about 2.6 millimeters. In one embodiment, the distance $D_1$ is about 1.314 millimeters. The diameter of the beam spot 154 may range from about 200 microns to about 2000 microns and more specifically, between about 400 microns to about 600 microns.

As the electromagnetic beam 52 enters the beam-shaping element 70, its optical path OP is folded by an angle $\beta$ from reflection off of the reflective element 114. In the depicted embodiment, the angle $\beta$ is approximately 90°, but in various embodiments can vary greater than or less than about 25°, about 20°, and about 10° on either side of 90°. The radius of curvature and position of the beam-shaping element 70 determine both the angle $\beta$ that the optical path OP of beam 52 will be folded by, and also a working distance $D_2$ to an image plane IMP where the beam 52 converges to form an image spot 160. Accordingly, the emitted beam 52 is shaped into the image spot 160 solely by reflection from the beam-shaping element 70.

Figure 6A:
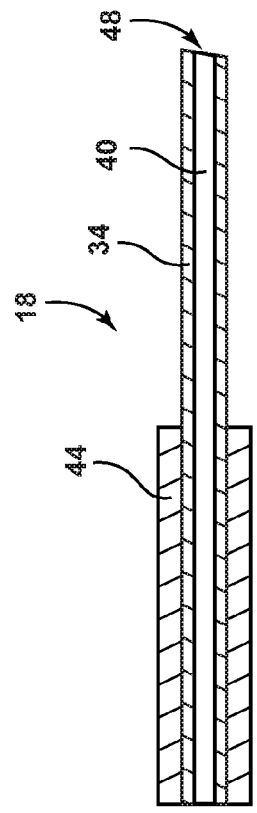
FIG. 6A is an enlarged view of the fiber employed in the probe of FIG. 1A according to one embodiment.
Figure 6B:
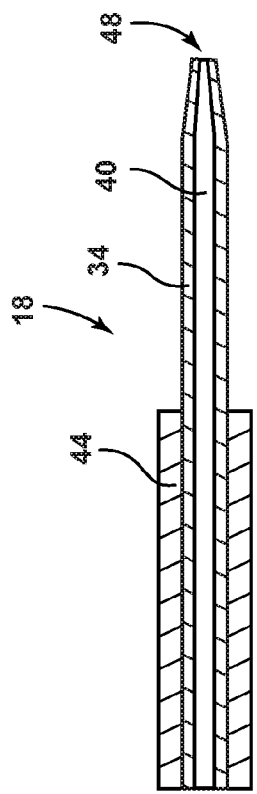
FIG. 6B is an enlarged view of the fiber employed in the probe of FIG. 1A according to another embodiment.
Figure 6C:
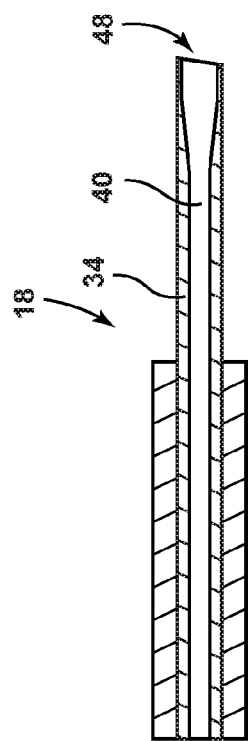
FIG. 6C is an enlarged view taken of the fiber employed in the probe of FIG. 1A according to yet another embodiment.

Referring now to FIGS. 5-6C, the fiber end 48 of the optical fiber 18 may terminate at an angle in order to prevent undesired back reflection of light into the fiber 18. OCT is particularly sensitive to back reflections of light which have not been scattered off of a sample to be tested (i.e., reflections from the optical probe 10, fiber end 48, or refractive surfaces along the optical path OP). The back reflected light may lead to increased noise and artifacts in the OCT image. Terminating the fiber end 48 at an angle minimizes the coupling of the back reflected light back into the optical fiber 18. The fiber end 48 may be prepared at an angle between about 0° to about 10° relative to an axis orthogonal to the longitudinal axis of the fiber, and more particularly between about 6° to 9°. Angling of the fiber end 48 may be accomplished, for example, by cleaving the fiber end 48 before or after insertion into the ferrule 62, or by polishing the face 150 of the ferrule 62 with the fiber end 48 at an angle, as depicted. In embodiments utilizing the monolithic body 120, the portion of the fiber end 48 protruding from the alignment feature 124 may simply be prepared with respect to the optical axis OA of the probe. In some embodiments, the ferrule 62 or beam-shaping element 70 may be angled with respect to the optical axis OA of the optical probe 10 in order to compensate for the angled fiber end 48. The angled ferrule 62 would keep the optical path OP of the beam 52 substantially coaxial with the optical axis OA of the optical probe 10. Additionally or alternatively, the fiber end 48 may include an anti-reflection film to reduce the amount of reflected light absorbed by the optical fiber 18. The anti-reflection film may include a single or multilayer dielectric material configured to cancel light reflected back to the optical probe 10. It will be understood that in embodiments incorporating the large fiber 144, the large fiber end 130A may be angled in the same or a substantially similar manner to that disclosed in connection with fiber end 48.

Referring now to FIGS. 6A-6C, various embodiments of the optical fiber 18 are depicted disembodied from the optical probe 10 and in cross-sectional form for purposes of clarity. As explained above and depicted in FIG. 6A, the fiber end 48 may simply be cleaved or otherwise angled to reduce back reflections.

Referring now to the depicted embodiment of FIG. 6B, the fiber end 48 of the optical fiber 18 is locally tapered to a reduced diameter with respect to the rest of the optical fiber 18. Tapering of the fiber end 48 may be accomplished through laser heating, plasma heating, resistance heating, or flame heating a portion of the optical fiber 18, and placing the fiber 18 in tension. The heated portion of the fiber 18 then necks down as it is pulled. The fiber 18 may be pulled until the fiber 18 is separated or the heated portion of the fiber 18 may be cut while in the necked down position.

Tapering of the core 40 may have an axial length along the optical fiber 18 of about 1 millimeter to about 5 millimeters, and in a specific example of about 4 millimeters. The tapering of the fiber end 48 should be such that the fiber end 48 does not experience adiabatic loss. Tapering of the optical fiber 18 at the fiber end 48 may locally increase the mode field diameter of the fiber end 48. The mode field diameter at a beam 52 wavelength of 1310 nanometers of the tapered fiber end 48 may range from about 10 microns to about 40 microns and in specific examples be about 10 microns, about 11 microns, about 12 microns, about 13 microns, about 14 microns, about 15 microns, about 16 microns, about 17 microns, about 18 microns, about 19 microns, or about 20 microns. The mode field diameter of the fiber end 48 may expand about 5%, about 10%, about 100%, about 400%, or about 500%. Tapering and angling the fiber end 48 of the optical fiber 18 may decrease the back reflection from about −10 dB to about −150 dB, and in specific examples to below about −80 dB, −90 dB, −100 dB, −110 dB, −120 dB and below about −130 dB depending on the level of tapering and the angle of the fiber end 48. Additionally or alternatively, the fiber end 48 may be tapered and positioned at locations other than at the face 150 of the ferrule 62. For example, a second optical fiber having similar dimensions to that of the tapered fiber end 48 may be positioned in the aperture 98 of the ferrule 62 and be optically coupled to the fiber end 48. In such embodiments, the optical coupling may take place at any point along the aperture 98 (e.g., inside the ferrule 62) as well as at the entrance to the aperture 98. The second optical fiber may then have an angled end, from which the electromagnetic beam 52 exits, to reduce back reflection. It will be understood that in embodiments incorporating the large fiber 144, the large fiber end 130A may be angled and/or include a locally expanded core in the same or a substantially similar manner to that disclosed in connection with fiber end 48.

Referring now to the depicted embodiment of FIG. 6C, the core 40 of the fiber end 48 has been locally expanded to an enlarged diameter in addition to being prepared with an angle. The core 40 of the optical fiber 18 may be locally expanded at the fiber end 48 such that the mode field diameter of the fiber 18 locally increases. In expanded core 40 embodiments, the fiber end 48 may have a mode field diameter at a beam 52 wavelength of 1310 nanometers between about 10 microns to about 40 microns with specific examples being about 10 microns, about 11 microns, about 12 microns, about 13 microns, about 14 microns, about 15 microns, about 16 microns, about 17 microns, about 18 microns, about 19 microns, and about 20 microns. The mode field diameter and diameter of the core 40 of the fiber end 48 may expand by about 5%, about 10%, about 100%, about 400%, or about 500%. Local expansion of the core 40 within the fiber end 48 may take place via laser heating, plasma heating, resistance heating, or flame heating a portion of an optical fiber and allowing sufficient time to pass for a portion of the core 40 to diffuse into the cladding 34. Expansion of the core 40 may have an axial length along the optical fiber 18 of about 1 millimeter to about 5 millimeters, and in a specific example of about 4 millimeters. Expanding the core 40 and angling the fiber end 48 of the optical fiber 18 may decrease the back reflection from about −10 dB to about −150 dB, and in specific examples to below about −80 dB, −90 dB, −100 dB, −110 dB, −120 dB and below about −130 dB. Additionally or alternatively, the core 40 of the fiber end 48 may be expanded and positioned at locations other than at the face 150 of the ferrule 62. For example, a second optical fiber having similar dimensions to that of the expanded core 40 fiber end 48 may be positioned in the aperture 98 of the ferrule 62 and be optically coupled to the fiber end 48. In such embodiments, the optical coupling may take place at any point along the aperture 98 (e.g., inside the ferrule 62) as well as at the entrance to the aperture 98. The second optical fiber may then have an angled end, from which the electromagnetic beam 52 exits, to reduce back reflection. It will be understood that in embodiments incorporating the large fiber 144, the large fiber end 130A may be angled and/or include a locally expanded core in the same or a substantially similar manner to that disclosed in connection with fiber end 48.

Figure 7A:
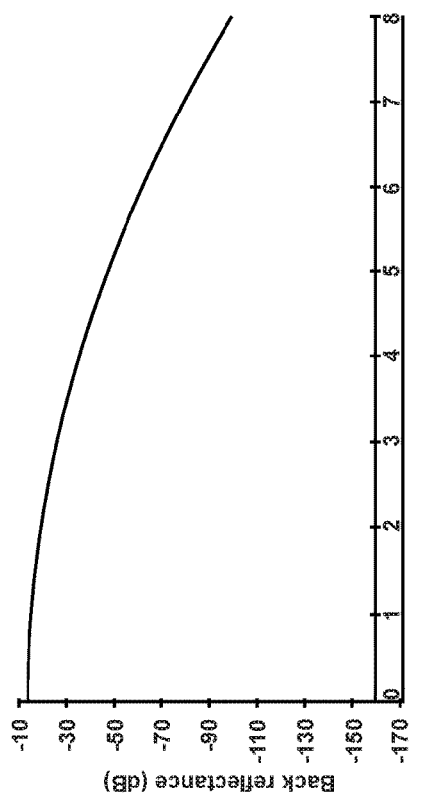
FIG. 7A is a graph showing the relationship between fiber end angle and back reflectance according to one embodiment.
Figure 7B:
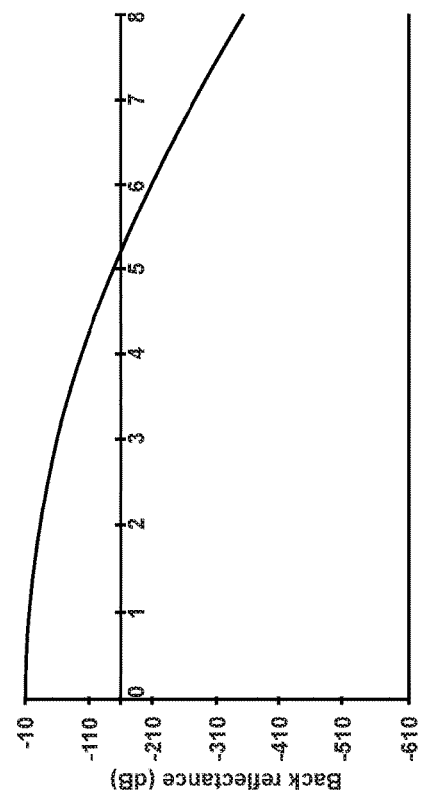
FIG. 7B is a graph showing the relationship between fiber end angle and back reflectance according to another embodiment.

Referring now to FIGS. 7A and 7B, depicted are plots of back reflections experienced by the optical probe 18 having just an angled fiber end 48 (FIG. 6A) and embodiments of the optical fiber 18 wherein the fiber core 40 has been expanded and angled (FIG. 6B). As can be seen from the plots, introducing an expansion of the mode field diameter through diffusion of the core 40, in addition to angling the fiber end 48, drastically reduces the back reflections encountered by the optical fiber 18 relative to only angling the fiber end 48.

Figure 8:
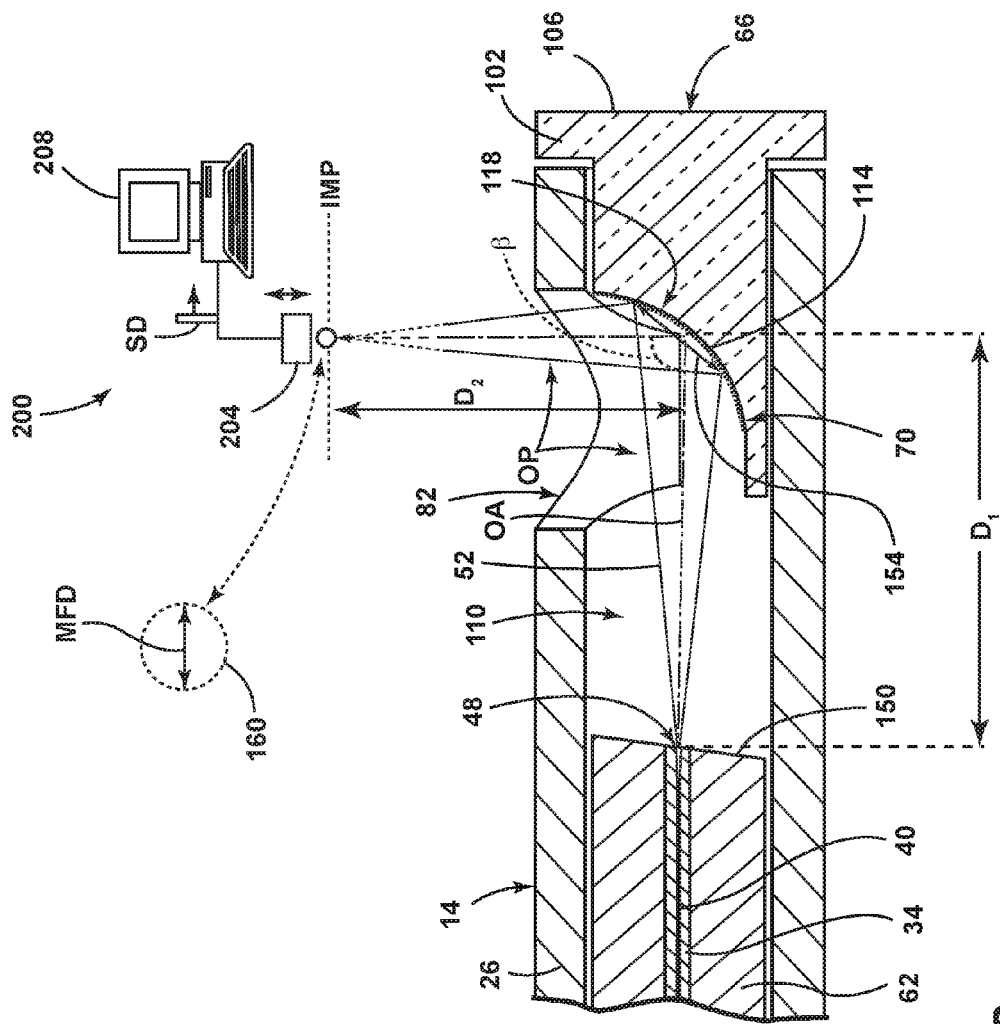
FIG. 8 is a schematic diagram of an OCT alignment system that includes the optical probe according to one embodiment.

Referring now to FIG. 8, the optical probe 10 is depicted in use within an OCT alignment system 200. As explained above, light traveling within the optical fiber 18 exits the fiber end 48 and is emitted as beam 52 along the optical axis OA. The optical path OP of the beam 52 diverges as it passes through the gap 110 until it enters the beam-shaping element 70 and reflects from the reflective element 114. The curvature of the beam-shaping element 70 causes the electromagnetic beam 52 to converge uniformly to the image spot 160 due to the curved surface 118 being conic. In the depicted embodiment, as the beam 52 converges, it passes through the window 82 of the sheath 14 and forms the image spot 160 at the image plane IMP. The working distance $D_2$ is measured between the horizontal portion of the optical axis OA of the probe and the image plane IMP and may be between about 1 millimeter and about 20 millimeters.

The proper orientation of the optical probe 10 during manufacturing is facilitated by the use of the ferrule 62, the beam-shaping insert 66, and the OCT alignment system 200. In an exemplary method for alignment of the optical fiber 18, a photodetector 204 (e.g., camera or a rotating slit) can be used to capture at least one image of image spot 160 and generate a detector signal SD representative of the captured image. The captured image(s) can be analyzed, e.g., via a computer 208 that is operably connected to photodetector 204. The computer 208 can be used to analyze and display information about the captured image spot(s) 160. In an example, a plurality of image spots 160 are detected and compared to a reference spot (e.g., as obtained via optical modeling based on the design of the optical probe 10) to assess performance. If the detected image spots 160 are incorrect, an operator assembling the optical probe 10 may adjust a distance in the Z direction between the first and second portions 22, 26 of the sheath 14, or use the markings on the forward surface 106 of the beam-shaping insert 66, to adjust its orientation relative to the sheath 14. The use of the ferrule 62 and the beam-shaping insert 66 allow for near precise alignment of the optical probe 10 upon initial assembly.

The mode field diameter (MFD) MFD is a measure of the spot size or beam width of light propagating in a single mode fiber or at another location in an optical system. The mode field diameter MFD within an optical fiber is a function of the source wavelength, fiber core radius and fiber refractive index profile. In the depicted embodiment, the optical probe 10 is capable of producing an image spot 160 having a mode field diameter MFD of between about 20 microns to about 100 microns at a $1/e^2$ threshold at the image plane IMP. An exemplary mode field diameter of the optical fiber 18 may be 9.2 microns at a $1/e^2$ threshold. The mode field diameter MFD may be sensed as an indicator of the quality of the image spot 160.

The position of optical fiber 18 can be axially adjusted within the optical probe 10 (e.g., by adjusting the first and second portions 22, 26 or moving the ferrule 62 or beam-shaping insert 66) based on making one or more measurements of image spot 160 until an acceptable or optimum image spot 160 is formed. In an example, the one or more measured image spots 160 are compared to a reference image spot or a reference image spot size. The ferrule 62 and the beam-shaping insert 66 can then be fixed in their respective aligned positions and orientations within the sheath 14 via one or more attachment methods (e.g., set screws, epoxies, adhesives, UV curable adhesives, friction fit, etc.).

In an exemplary embodiment of optical probe 10, the beam-shaping element 26 has an X-axis radius of curvature of about 1.16 millimeters and an X-axis conic constant of about 0.5858 and a Y-axis radius of curvature of about 1.2935 millimeters and a Y-axis conic constant of about 0.8235. Further, the conic shape of the beam-shaping element 70 is decentered along the Y-axis by about 0.7 millimeters, decentered along the Z-axis by about 0.089 millimeters, and has a rotation between the Y- and Z-axes of about 89.7°. The distance $D_1$ between the fiber end 40 and reflective element 114 is about 1.314 millimeters. Such an optical probe is capable of forming the image spot 160 at a working distance $D_2$ of about 9.0 millimeters with a mode field diameter MFD of about 64 microns at the $1/e^2$ threshold.

Because optical probe 10 and the exemplary optical coherence tomography alignment system 200 has a beam-shaping insert 66 which defines a reflective beam-shaping element 70, the system has no need for the use of spacers, GRIN lenses or refractive elements, such as lenses. Further, eliminating the use of multiple optical components is beneficial because there are fewer material interfaces which may result in optical back reflections or vignetting of the image spot 160. Additionally, by shaping the beam 52 into the image spot 160 solely based on reflection, higher power light sources may be used than conventional optical probes. Optical probes utilizing polymers as a refractive element are limited in the intensity of light they may refract; however, reflective systems do not have such limitations.

Figure 9:
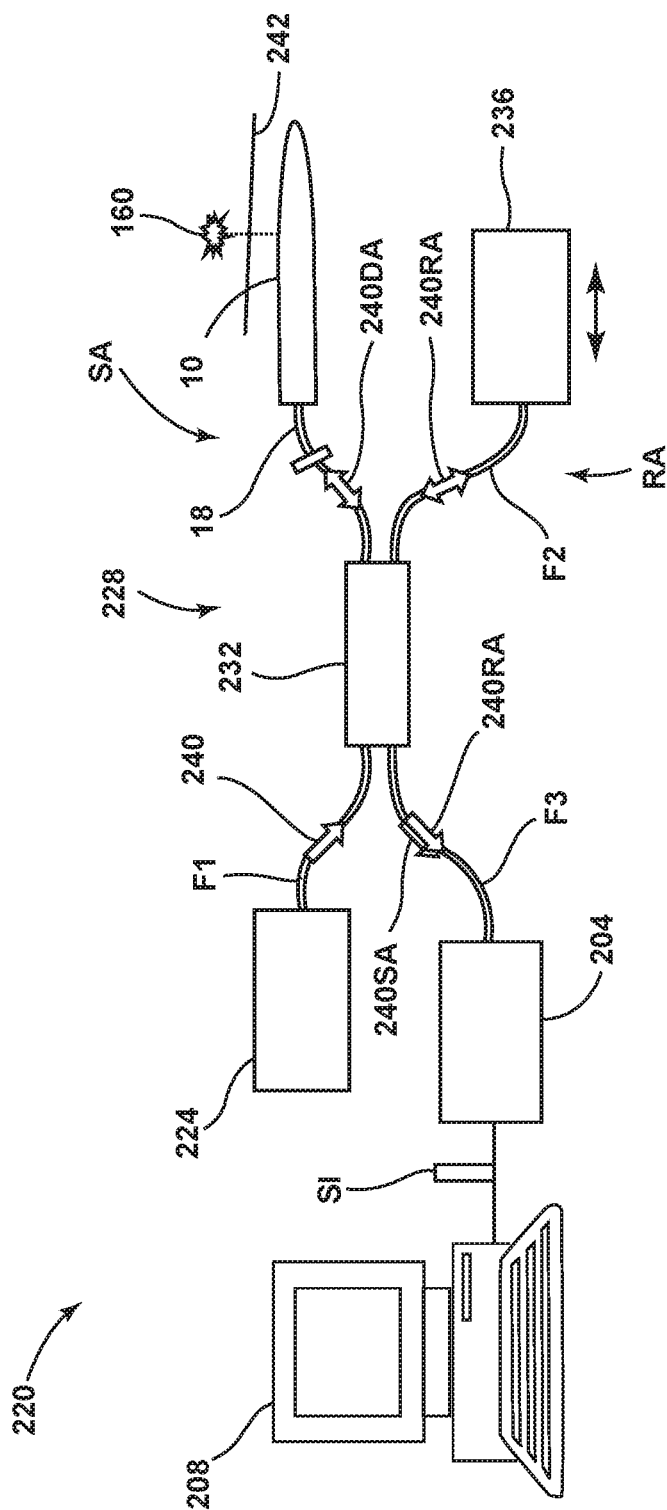
FIG. 9 is a schematic diagram of an OCT system that includes the optical probe according to one embodiment.

FIG. 9 illustrates an exemplary OCT system 220 that includes an embodiment of the optical probe 10 as disclosed herein. OCT system 220 includes a light source 224 and an interferometer 228. The light source 224 is optically connected to a fiber optic coupler ("coupler") 232 via a first optical fiber section FI. OCT probe 10 is optically connected to coupler 232 via optical fiber 18 and constitutes the sample arm SA of the interferometer 228. OCT system 220 also includes a movable mirror system 236 optically connected to coupler 232 via an optical fiber section F2. Mirror system 236 and optical fiber section F2 constitute a reference arm RA of the interferometer 228. Mirror system 236 is configured to alter the length of the reference arm, e.g., via a movable mirror (not shown). OCT system 220 further includes the photodetector 204 optically coupled to coupler 232 via a third optical fiber section F3. Photodetector 204 in turn is electrically connected to computer 208.

In operation, light source 224 generates light 240 that travels to interferometer 228 over optical fiber section FI. The light 240 is divided by coupler 232 into light 240RA that travels in reference arm RA and light 240SA that travels in sample arm SA. The light 240RA that travels in reference arm RA is reflected by mirror system 236 and returns to coupler 232, which directs the light to photodetector 204. The light 240SA that travels in sample arm SA is processed by optical probe 10 as described above (where this light was referred to as just emitted beam 52) to form image spot 160 on or in a sample 244. The resulting scattered light is collected by optical probe 10 and directed through optical fiber 18 to coupler 232, which directs it (as light 240SA) to photodetector 204. The reference arm light 240RA and sample arm light 240SA interfere and the interfered light is detected by photodetector 204. Photodetector 204 generates an electrical signal SI in response thereto, which is then sent to computer 208 for processing using standard OCT signal processing techniques.

The optical interference of light 240SA from sample arm SA and light 240RA from reference arm RA is detected by photodetector 204 only when the optical path difference between the two arms is within the coherence length of light 240 from light source 224. Depth information from sample 244 is acquired by axially varying the optical path length of reference arm RA via mirror system 236 and detecting the interference between light from the reference arm and scattered light from the sample arm SA that originates from within the sample 244. A three-dimensional image is obtained by transversely scanning in two dimensions the optical path in the sample arm SA. The axial resolution of the process is determined by the coherence length.

It should be understood that although the use of the optical probe 10 was described in connection with only one OCT technique, the optical probe 10 may be used in a wide variety of applications, including other OCT techniques (e.g., Frequency Domain OCT, Spectral Domain OCT).

While the embodiments disclosed herein have been set forth for the purpose of illustration, the foregoing description should not be deemed to be a limitation on the scope of the disclosure or the appended claims. It will be apparent to those skilled in the art that various modifications and variations can be made without departing from the spirit or scope of the claims.

It will be understood by one having ordinary skill in the art that construction of the described invention and other components is not limited to any specific material. Other exemplary embodiments of the invention disclosed herein may be formed from a wide variety of materials, unless described otherwise herein. In this specification and the amended claims, the singular forms "a," "an," and "the" include plural reference unless the context clearly dictates otherwise.

Where a range of values is provided, it is understood that each intervening value, to the tenth of the unit of the lower limit, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It will be apparent to those skilled in the art that various modifications and variations can be made without departing from the spirit or scope of the claims.

What is claimed is:

1. A beam-shaping optical system suitable for use with optical coherence tomography, comprising: a sheath defining a central cavity; a beam-shaping insert defining a beam-shaping element positioned within the central cavity, the beam-shaping insert having a flange in abutting contact with a distal end of the sheath; and an optical fiber having a core and a cladding, the optical fiber defining an angularly prepared fiber end configured to emit an electromagnetic beam toward the beam-shaping element, wherein the core of the optical fiber has at least one of a locally expanded core at the fiber end or the fiber end is tapered.

2. The beam-shaping optical system of claim 1, wherein the angle of the fiber end has an angle between about 4° and about 10°.

3. The beam-shaping optical system of claim 1, wherein the fiber end is configured to have a back reflection less than about −75 db.

4. The beam-shaping optical system of claim 1, wherein the locally expanded core of the optical fiber has a mode field diameter of between about 10 microns and about 40 microns at a beam wavelength of about 1310 nanometers.

5. The beam-shaping optical system of claim 1, wherein the optical fiber is positioned with a ferrule and the fiber end is positioned at a face of the ferrule.

6. The beam-shaping optical system of claim 5, wherein the face of the fiber end is flush with the face of the ferrule such that the face is disposed at the same angle as the fiber end.

7. The beam-shaping optical system of claim 1, wherein the ferrule and the beam-shaping insert are configured to concentrically mate with the sheath such that the ferrule and the beam-shaping insert are each flush with an inner surface of the sheath.

8. The beam-shaping optical system of claim 1, wherein the beam-shaping element is defined from a curved surface of the beam-shaping body and comprises at least one of a dielectric, metal, and enhanced metal coating and the beam-shaping element has a radius of curvature between about 1.0 millimeters and about 4.0 millimeters.

9. An optical coherence tomography probe, comprising: a sheath defining a central cavity; an optical fiber having a core and a cladding positioned within a ferrule, the ferrule positioned within the central cavity; and an electromagnetic beam emitted from a fiber end of the optical fiber toward a beam-shaping element, wherein the optical fiber has at least one of an expanded core at the fiber end or the fiber end is tapered relative to the optical fiber to produce a mode field diameter of between about 10 microns and about 40 microns at a beam wavelength of 1310 nanometers; wherein the beam-shaping element is defined from a beam-shaping insert which is configured to concentrically engage the central cavity of the sheath, the beam-shaping insert having a flange in abutting contact with a distal end of the sheath.

10. The optical coherence tomography probe of claim 9, wherein the fiber end of the optical fiber is prepared at an angle between about 4° and about 10°.

11. The optical coherence tomography probe of claim 10, wherein the fiber end is positioned to be flush with a face of the ferrule.

12. The optical coherence tomography probe of claim 9, wherein the optical fiber is a single mode optical fiber.

13. The optical coherence tomography probe of claim 12, wherein the back reflection is less than about −65 dB.

14. The optical coherence tomography probe of claim 13, wherein the fiber end is optically coupled to a second optical fiber located inside of the ferrule.

15. A method of operating an optical coherence tomography probe using an optical fiber, comprising the steps: positioning an optical fiber with an expanded core or tapered end within a central cavity of a sheath; positioning a beam-shaping element within the sheath such that a flange of the beam-shaping element engages the distal end of the sheath; transmitting an electromagnetic beam from a fiber end of the optical fiber into the beam-shaping element; and receiving a back reflection from the electromagnetic beam of less than about −100 dB.

16. The method of operating an optical coherence tomography probe of claim 15, wherein the fiber end of the optical fiber is prepared at an angle between about 4° and about 10°.

17. The method of operating an optical coherence tomography probe of claim 16, wherein the fiber end has a tapered configuration.

18. The method of operating an optical coherence tomography probe of claim 16, wherein the fiber end includes a locally expanded core.

19. The method of operating an optical coherence tomography probe of claim 18, wherein the beam-shaping element is defined on a beam-shaping insert, the beam-shaping insert configured to engage the central cavity of the sheath in a substantially concentric manner.

20. An optical coherence tomography probe, comprising: a sheath defining a central cavity and an opening; an optical fiber having a core with an expanded core or tapered end and a cladding positioned within a ferrule, the ferrule positioned within the central cavity of the sheath; a flange of a beam shaping element that engages the distal end of the sheath; and a torque tube having an exterior surface and a solid end, the solid end having a reduced portion configured to mate with the opening.

21. The optical coherence tomography probe of claim 20, wherein the sheath defines a sheath surface and the torque tube defines an exterior surface, further wherein the sheath surface and the exterior surface are substantially flush with one another.

22. The optical coherence tomography probe of claim 20, wherein the reduced portion of the solid end is positioned within the central cavity.

23. The optical coherence tomography probe of claim 20, wherein the solid end and the reduced portion are cylindrical and wherein the reduced portion has an outside diameter smaller than an outside diameter of the solid end.

24. The optical coherence tomography probe of claim 20, further comprising: a beam-shaping insert, the beam-shaping insert positioned within the central cavity and defining a beam-shaping element.

25. The optical coherence tomography probe of claim 24, wherein the optical fiber defines a fiber end configured to emit an electromagnetic beam toward the beam-shaping element.

* * * * *